United States Patent [19]

Ryan

[11] Patent Number: 4,929,773
[45] Date of Patent: May 29, 1990

[54] METHOD OF PRODUCING 1-(4'-ISOBUTYLPHENYL)ETHANOL

[75] Inventor: Debra A. Ryan, Corpus Christi, Tex.

[73] Assignee: Hoechst Celanese Corporation, Somerville, N.J.

[21] Appl. No.: 242,082

[22] Filed: Sep. 7, 1988

[51] Int. Cl.$^5$ ............... C07C 29/14; C07C 29/132
[52] U.S. Cl. ........................ 568/814; 568/846; 568/861; 568/862
[58] Field of Search ............ 568/814, 846, 861, 862

[56] References Cited

U.S. PATENT DOCUMENTS 4,273,933  6/1981  Harada et al. ............... 568/814

FOREIGN PATENT DOCUMENTS

CS 219752   9/1985  Czechoslovakia .
55-027147   2/1980  Japan .
0035064     3/1980  Japan ............... 568/814
2185032     8/1987  Japan ............... 568/814

OTHER PUBLICATIONS

D. P. Curran, J. Am. Chem. Soc. 1983, 105, 5826–5833.
M. Delepine et al., Bull. Soc. Chim. France, 1937, 31–49.
M. Freifelder et al., J. Pharm. Sci. 53, 967 (1964).
M. Freifelder, *Catalytic Hydrogenation in Organic Synthesis–Procedures and Commentary*, John Wiley, New York (1978), pp. 81–89.
L. Kotlyarevskii et al., Khim. Prom., 1981 (7), 391–393 Translated in Soviet Chemical Industry, 13:7, 813–819 (1981).
D. Nightingale et al., J. Org. Chem. 14, 1089–1093 (1949).
G. G. Hawley, *Condensed Chemical Dictionary*, 10th Ed., Van Nostrand Reinhold, New York (1959), p. 883.
M. Windholz, Ed., *The Merck Index*, 10th Ed., Merck & Co., Rahway, NJ (1983), p. 8019.

Primary Examiner—Werren B. Lone
Attorney, Agent, or Firm—D. R. Cassady

[57] ABSTRACT

A method is provided for the production of 1-(4'-isobutylphenyl)ethanol (IBPE) comprising hydrogenating 4-isobutylacetophenone (IBAP) in the absence of a solvent using as a catalyst a treated activated sponge nickel catalyst, e.g., Raney nickel, obtained by subjecting such a catalyst wetted with a protective liquid composed preponderantly of water to a washing treatment with an organic washing liquid in which the aqueous protective liquid is substantially soluble and which is substantially soluble in IBAP or IBPE, e.g., a lower alkanol such as methanol, ethanol or isopropanol. The catalyst optionally may also be washed with IBAP or IBPE after the wash with the organic washing liquid and before being used in the hydrogenation reaction. The washing treatment results in substantially higher conversions IBAP and increased yields of IBPE with a practical reaction time.

9 Claims, No Drawings

METHOD OF PRODUCING 1-(4'-ISOBUTYLPHENYL)ETHANOL

BACKGROUND OF THE INVENTION

1. Field of the Invention

This invention relates to a new method of producing 1-(4'-isobutylphenyl)ethanol (IBPE).

2. Background Information

The compound 2-(4'-isobutylphenyl)propionic acid, more commonly known as ibuprofen, is a well-known nonsteroidal anti-inflammatory drug which has been converted from ethical, i.e., prescription, to over-the-counter status.

A recently proposed method of producing ibuprofen is disclosed in pending U.S. patent application Ser. No. 028,514, filed Mar. 20, 1988, by Elango et al, involves the carbonylation of IBPE under prescribed conditions using any of certain palladium-containing catalysts. Also disclosed in this application is the preparation of IBPE by the hydrogenation of 4-isobutylacetophenone (IBAP) using any of various hydrogenation catalysts, including Raney nickel.

Activated sponge nickel, e.g., Raney nickel, which is a widely used type of hydrogenation catalyst, is pyrophoric, i.e., it tends to ignite spontaneously in the presence of air. Because of this, it is stored and shipped submerged in a liquid which effectively protects it from contact with air. The most common type of protective liquid used for this purpose is composed preponderantly of water, e.g., water containing a small amount of dissolved alkaline material, e.g., sodium hydroxide.

3. Description of Related Art

The following information is disclosed in accordance with the terms of 37 CFR 1.56, 1.97 and 1.98.

Japanese Kokai Patent No. SHO 55 [1980]-27147, published Feb. 27, 1980, and assigned to Mitsubishi Petrochemical Co., discloses the formation of aryl-substituted carboxylic acids, e.g., ibuprofen, by reacting an aryl-substituted alcohol, e.g., IBPE, with carbon monoxide and water in the presence of a hydrogen fluoride catalyst. Also disclosed generally is the synthesis of the aryl-substituted alcohol by reducing the corresponding ketone.

Czech Patent No. CS 219,752 of Sept. 15, 1985, discloses a process of making ibuprofen from isobutylbenzene including the step of reducing IBAP to IBPE using lithium aluminum hydride as reductant.

D. P. Curran, J. Am. Chem. Soc. 1983, 105, 5826–5833, discloses the reduction of isoxazolines to beta-hydroxy ketones using Raney nickel as catalyst and aqueous methanol as solvent. The washing of Raney nickel free of hydroxide with 20-30 water washes prior to use is shown on page 5830.

M. Delepine et al, Bull. Soc. Chim. France, 1937, 31–49, teach the preparation of aromatic carbinols such as methylphenylcarbinol and ethylphenylcarbinol by hydrogenation of the corresponding ketone using Raney nickel promoted with alkali as catalyst, and ethyl alcohol as solvent.

M. Freifelder et al, J. Pharm. Sci. 53, 967 (1964), teach the preparation of 1-phenylethanol by hydrogenation of acetophenone using Raney nickel promoted with alkali as catalyst and ethyl alcohol as solvent.

M. Freifelder, *Catalytic Hydrogenation in Organic Synthesis—Procedures and Commentary*, John Wiley, New York (1978), pages 81–89, discloses the use of Raney nickel as catalyst for the hydrogenation of various aromatic aldehydes and ketones to the corresponding alcohols, e.g., acetophenone to 1-phenyl-1-ethanol in ethyl alcohol as solvent. On page 83, the reference states that Raney nickel "may well be the one of choice for the reduction of aromatic aldehydes and ketones . . ."

L. Kotlyarevskii et al, Khim. prom., 1981 (7), 391–393, translated in Soviet Chemical Industry, 13:7, 813–819 (1981), disclose a process of synthesizing p-divinylbenzene, including the step of reducing p-diacetylbenzene (p-DAB) using Raney nickel as catalyst, to produce "1-4-bis(α-oxyethyl)benzene."

D. Nightingale et al, J. Org. Chem. 14, 1089–1093 (1949), teach at page 1090 the hydrogenation of various aromatic ketones using Raney nickel as catalyst to produce the corresponding carbinol and aromatic hydrocarbon.

G. G. Hawley, *Condensed Chemical Dictionary*, 10th Ed., Van Nostrand Reinhold, New York (1959), page 883, and M. Windholz, Ed., *The Merck Index*, 10th Ed., Merck & Co., Rahway, NJ (1983), p. 8019, show that Raney nickel is pyrophoric and is generally stored under a protective liquid such as water.

SUMMARY OF THE INVENTION

In accordance with this invention, 1-(4,'-isobutylphenyl)ethanol (IBPE) is produced by hydrogenating 4-isobutylacetophenone (IBAP) with hydrogen in the absence of a solvent using as a catalyst a treated activated sponge nickel catalyst, e.g., Raney nickel, obtained by subjecting such a catalyst wetted with a protective liquid composed preponderantly of water to a washing treatment with an organic washing liquid in which the aqueous protective liquid is substantially soluble, such washing liquid being substantially soluble in IBAP or IBPE. Such a washing treatment has the effect of substantially increasing the conversion of IBAP and yield of IBPE within a practical reaction time. After the treatment of the catalyst with organic washing liquid, it may be optionally washed with IBAP or IBPE which, in most cases, has the effect of reducing the contamination of the IBPE product with organic washing liquid. Note that, in accordance with any of the foregoing treatments, the catalyst is not permitted to become exposed to the air in the absence of any protective liquid at all. Thus, while the catalyst is initially wetted with a protective liquid composed preponderantly of water, it is finally utilized in the process wetted with organic washing liquid, IBAP or IBPE, each of which is effective in preventing the catalyst from igniting on contact with air.

DESCRIPTION OF PREFERRED EMBODIMENTS

Activated sponge nickel catalysts, e.g., Raney nickel, are a well-known class of materials effective for various hydrogenation reactions. They are prepared by treating an alloy of approximately equal amounts by weight of nickel and aluminum with an aqueous alkali solution, e.g., containing about 25 wt. % of sodium hydroxide. The aluminum is selectively dissolved by the aqueous alkali solution leaving particles having a sponge construction and composed predominantly of nickel with a minor amount of aluminum. Promotor metals such as molybdenum or chromium may be also included in the initial alloy in an amount such that about 1-2 wt. % remains in the sponge nickel catalyst. These catalysts also contain surface hydrogen which causes them to ignite if exposed to air without being coated with a protective liquid, e.g., composed preponderantly of water, as contemplated for treatment under this invention. Protective liquids of the latter type most commonly used are aqueous alkaline solutions, e.g., of sodium hydroxide, having a pH of about 9.5–10.5, in view of its relative cheapness and safety.

Organic washing liquids useful in the method of this invention in which the protective liquid on the catalyst is substantially soluble, and which are substantially soluble in IBAP or IBPE, are, for example, lower alkanols containing one to three carbon atoms, e.g., methanol, ethanol, or isopropanol, cyclic ethers such as tetrahydrofuran, dioxane-1,4, dioxane-1,3, and diethers and monoethers of ethylene glycol and diethylene glycol such as ethylene glycol dimethyl ether, diethylene glycol dimethyl ether, ethylene glycol monomethyl ether and ethylene glycol monoethyl ether.

The term "substantially soluble" in the foregoing discussion means, for example, capable of dissolving in the stated solvent in an amount of at least about 50 wt. % based on the weight of the solution in the stated solvent. Preferably, the washing liquid is completely miscible with the protective liquid and IBAP or IBPE.

The washes with the organic washing agent and, if utilized, IBAP or IBPE, are accomplished, for example, by stirring or agitating the nickel catalyst with an amount of the washing liquid sufficient to wet all of the nickel particles, e.g., for a period of about 1 to 5 minutes in the case of 500 g of catalyst, and decanting the excess washing liquid. While this may be done once for each washing liquid, it is preferably done at least 2 or 3 times. In most cases, the washes may be carried out at room temperature, although elevated temperatures may be utilized to obtain the desired solubilities.

The hydrogenation of IBAP to form IBPE is accomplished by contacting IBAP and hydrogen in the absence of a solvent with an activated sponge nickel catalyst treated as described previously. The catalyst may be used in an amount, for example, of about 1% to 30 wt. %, preferably about 3 to 20 wt. %, based on the weight of the total reaction mass. In carrying out the reaction, the hydrogen pressure may be in the range, for example, of about 10 to 1200 psig, preferably about 200 to 1000 psig; the reaction temperature may be in the range, for example, of about 10° to 150° C., preferably about 40° to 80° C.; and the reaction time may be in the range, for example, of about 0.25 to 10.0 hours, preferably about 1.0 to 4.0 hours.

The following examples further illustrate the invention.

EXAMPLES 1 to 13

In these examples, a weighed amount of an activated sponge nickel catalyst composed of particles having an average dimension of about 25 to 45 microns and slurried in alkaline water having a pH of about 9.5–10.5 in which it was stored, was transferred to a mixing vessel, using a small amount of deionized water to aid in the transfer. An approximately equal volume of isopropanol or ethanol was added to the vessel and the contents were mixed using an overhead mixer. The catalyst was allowed to settle and the alcohol/water layer decanted using a magnet to aid in the decanting. The alcohol wash was repeated in a similar fashion two more times. In some examples, the catalyst was then similarly washed three times in either the reactant IBAP or the product IBPE.

The catalyst slurried in the last batch of wash liquid was then charged to a stirred autoclave and a weighed amount of IBAP was also charged. The autoclave was sealed, purged of air with nitrogen, and pressure checked, and hydrogen was introduced. Stirring was begun, the autoclave was heated to maintain a desired reaction temperature, and hydrogen was fed on demand to maintain a desired reaction pressure. When hydrogen uptake had ceased marking the end of the reaction, the autoclave was cooled 10°–15° C., the hydrogen vented, and the autoclave purged with nitrogen. The IBPE product was filtered from the catalyst and analyzed by gas chromatography.

The catalyst used in the examples were all activated sponge nickel catalysts as described previously and were considered equivalent for the purpose of carrying out the method of this invention, although obtained from different sources as follows: Raney Active Metal Catalysts R3100 (Examples 1 to 7), R3200 (Example 12) and R2400 (Example 13), all obtained from Davison Chemical Division of W. R. Grace & Co., Activated Nickel Catalyst BK111W (Example 8) and BK113W (Examples 9 and 10) obtained from Degussa Corp., and Sponge Metal Catalyst A7100 (Example 11) obtained from Activated Metals & Chemicals, Inc. All the catalysts contained about 1% of molybdenum as a promotor except R2400 (Example 13) which contained 1–2% chromium.

The conditions and results are shown in the table which indicates the mode of washing of the catalyst (Cat. Wash.), i.e., isopropanol only (IPA), ethanol only (EtOH), isopropanol and IBAP (IPA/IBAP) or isopropanol and IBPE (IPA/IBPE), the amount of catalyst utilized as a percent of the total dry weight of the reaction mass, i.e., calculated on a dry basis (Cat. Amt.), the reaction pressure (Press.), the reaction temperature (T), the reaction time (t), the percent conversion of IBAP (conv.) and analyses of the product in terms of weight percents of IBAP, IBPE, isopropanol (IPA) and water ($H_2O$). The catalyst of Example 1 was used in Example 2 without any further washing, and the weight percent of IBPE in all products includes both 1-(4'-isobutylphenyl)ethanol and 1-(3'-isobutylphenyl)ethanol, although the latter isomer was never more than about 3% of the total of the two isomers.

TABLE

| Ex. | Cat. Wash | Cat. Amt. wt % | Press. psig | T °C. | t min. | Conv. % | Product Analysis, wt % |||| 
|---|---|---|---|---|---|---|---|---|---|---|
| | | | | | | | IBAP | IBPE | IPA | $H_2O$ |
| 1 | IPA/IBAP | 10.2 | 250 | 60 | 97 | 99.9 | 0.14 | 96.9 | 0.11 | 0.34 |
| 2 | IPA/IBAP | 10.2 | 250 | 60 | 103 | 99.7 | 0.03 | 96.1 | 0.00 | 0.17 |
| 3 | IPA | 10.0 | 250 | 60 | 77 | 99.7 | 0.26 | 95.8 | 2.66 | 0.52 |
| 4 | IPA/IBPE | 7.5 | 250 | 60 | 90 | 99.8 | 0.22 | 97.6 | 1.30 | 0.59 |
| 5 | IPA | 10.1 | 500 | 75 | 75 | 99.4 | 0.56 | 91.8 | 2.70 | 0.39 |
| 6 | IPA | 5.8 | 500 | 75 | 170 | 99.5 | 0.45 | 94.2 | 1.58 | 0.44 |
| 7 | IPA | 10.5 | 1000 | 55 | 95 | 99.5 | 0.52 | 90.9 | 2.80 | 0.69 |
| 8 | IPA | 10.4 | 250 | 60 | 222 | 99.8 | 0.16 | 82.9 | 5.56 | 0.98 |

TABLE-continued

| Ex. | Cat. Wash | Cat. Amt. wt % | Press. psig | T °C. | t min. | Conv. % | Product Analysis, wt % | | | |
|---|---|---|---|---|---|---|---|---|---|---|
| | | | | | | | IBAP | IBPE | IPA | H$_2$O |
| 9 | IPA/IBAP | 10.4 | 250 | 60 | 203 | 99.7 | 0.28 | 88.7 | 0.11 | 0.73 |
| 10 | IPA/IBPE | 7.5 | 250 | 60 | 145 | 99.4 | 0.55 | 86.5 | 1.90 | 1.30 |
| 11 | IPA/IBPE | 7.6 | 250 | 60 | 148 | 98.7 | 1.26 | 80.8 | 0.92 | 1.64 |
| 12 | IPA | 10.5 | 250 | 60 | 198 | 99.7 | 0.29 | 90.0 | 5.44 | 0.78 |
| 13 | EtOH | 10.0 | 350 | 65 | 145 | 91.5 | 8.40 | 85.7 | — | — |

COMPARATIVE EXAMPLE

The conditions of Example 1 were followed except that the catalyst wet with alkaline water as a protective liquid was not washed with isopropanol or IBAP and the amount of catalyst in the reaction mass was 10.1 rather than 10.2 wt. %. Moreover, in attempting to increase the conversion of IBAP, a reaction temperature of 75°–85° C. was utilized and the reaction was continued for 240 min, longer than in any of Examples 1 to 13. Nevertheless, the IBAP conversion was only 13.7% and the product contained 84.1 wt. % of IBAP, 9.1 wt. % of IBPE and 0.73 wt. % of H$_2$O.

The results of Examples 1 to 13 as shown in the Table and of the comparative example indicate that high conversions of IBAP and products containing high percentages of desired IBPE are obtained utilizing the washing procedure of this invention. Moreover, when an IBAP or IBPE wash is carried out after the wash with organic washing liquid, e.g., isopropanol, the product in most cases is less contaminated with organic washing liquid than when no IBAP or IBPE wash is included.

When an activated sponge nickel catalyst stored in alkaline water was used for the hydrogenation of IBAP to IBPE without the washing treatment of this inventory, the conversion of IBAP and yield of IBPE fell drastically, as shown by the results of the foregoing Comparative Example.

I claim:

1. A method of producing 1-(4′-isobutylphenyl)ethanol (IBPE) comprising hydrogenating 4-isobutylacetophenone (IBAP) with hydrogen in the absence of a solvent using a treated activated sponge nickel catalyst obtained by subjecting such a catalyst wetted with a protective liquid composed preponderantly of water to a washing treatment with an organic washing liquid in which the aqueous protective liquid is substantially soluble, such washing liquid being substantially soluble in IBAP or IBPE.

2. The method of claim 1 wherein said organic washing liquid is methanol, ethanol or isopropanol.

3. The method of claim 2 wherein after the washing with said organic washing liquid, the still wet catalyst is washed with IBAP.

4. The method of claim 2 wherein after the washing with said organic washing liquid, the still wet catalyst is washed with IBPE.

5. The method of claim 2 wherein said organic washing liquid is isopropanol.

6. The method of claim 1 wherein the conditions of said hydrogenation include an amount of catalyst of about 1 to 30 wt. % based on the total weight of reactor mass, a hydrogen pressure of about 10 to 1200 psig, a reaction temperature of about 10° to 150° C., and a reaction time of about 0.25 to 10 hours.

7. The method of claim 1 wherein said organic washing liquid is a lower alkanol containing one to three carbon atoms, tetrahydrofuran, dioxane-1,4, dioxane-1,3, or a diether or monoether of ethylene glycol or diethylene glycol.

8. The method of claim 2 wherein said organic washing liquid is the only compound present during said washing treatment.

9. The method of claim 7 wherein said organic washing liquid is the only organic compound present during said washing treatment.

* * * * *